US011179070B2

(12) United States Patent
Bien

(10) Patent No.: US 11,179,070 B2
(45) Date of Patent: Nov. 23, 2021

(54) GLUCOSE MEASUREMENT DEVICE AND METHOD

(71) Applicant: UNIST (ULSAN NATIONAL INSTITUTE OF SCIENCE AND TECHNOLOGY), Ulsan (KR)

(72) Inventor: Franklin Don Bien, Ulsan (KR)

(73) Assignee: UNIST (Ulsan National Institute of Science and Technology), Ulsan (KR)

( * ) Notice: Subject to any disclaimer, the term of this patent is extended or adjusted under 35 U.S.C. 154(b) by 0 days.

(21) Appl. No.: 17/195,424

(22) Filed: Mar. 8, 2021

(65) Prior Publication Data

US 2021/0186386 A1 Jun. 24, 2021

Related U.S. Application Data

(63) Continuation of application No. PCT/KR2020/005334, filed on Apr. 22, 2020.

(30) Foreign Application Priority Data

May 24, 2019 (KR) .......................... 10-2019-0061153
Apr. 21, 2020 (KR) .......................... 10-2020-0048191

(51) Int. Cl.
*A61B 5/145* (2006.01)
*H03L 7/08* (2006.01)
*A61B 5/00* (2006.01)
*H02J 50/10* (2016.01)

(52) U.S. Cl.
CPC ........ *A61B 5/14532* (2013.01); *A61B 5/0022* (2013.01); *A61B 5/14503* (2013.01);
(Continued)

(58) Field of Classification Search
CPC ....... A61B 5/145; A61B 5/00; A61B 5/14503; A61B 5/0022; A61B 5/14532;
(Continued)

(56) References Cited

U.S. PATENT DOCUMENTS 10,478,101 B1 * 11/2019 Cespedes ........... A61B 5/14532
2013/0141117 A1   6/2013 Nikolenko
(Continued)

FOREIGN PATENT DOCUMENTS

GB        2428801 A    2/2007
KR   1020050011166 A   1/2005
(Continued)

OTHER PUBLICATIONS

International Search Report dated Jul. 28, 2020, issued in corresponding Application No. PCT/KR2020/005334, filed Apr. 22, 2020, 6 pages.
(Continued)

*Primary Examiner* — Eric J Messersmith
(74) *Attorney, Agent, or Firm* — Christensen O'Connor Johnson Kindness PLLC

(57) ABSTRACT

The present invention relates to a glucose measurement device which is arranged and operates under the skin of a subject. One embodiment can comprise: a transmitting unit for wirelessly receiving power and transmitting measured biometric-related parameters; a clock recovery unit for recovering a frequency used for the wireless power reception of the communication unit; a direct frequency synthesizer for converting the recovered frequency recovered by the clock recovery unit into a first band frequency; a clock control unit, which divides the recovered frequency so as to input same in an injection locked oscillator as a specific interval frequency; the injection locked oscillator, which receives the first band frequency and the specific interval frequency so as to output a second band frequency; and a measurement unit for measuring subcutaneous biometric-related parameters by using the second band frequency.

9 Claims, 7 Drawing Sheets

(52) U.S. Cl.
CPC .... *H03L 7/0807* (2013.01); *A61B 2560/0214* (2013.01); *H02J 50/10* (2016.02)

(58) Field of Classification Search
CPC . A61B 2560/0214; H03L 7/08; H03L 7/0807; H02J 50/10
See application file for complete search history.

(56) References Cited

U.S. PATENT DOCUMENTS

| | | | |
|---|---|---|---|
| 2016/0338625 A1* | 11/2016 | Min | A61B 5/14532 |
| 2017/0230084 A1* | 8/2017 | Zhu | H04B 5/0093 |
| 2018/0247095 A1 | 8/2018 | Sundaram et al. | |
| 2020/0169300 A1* | 5/2020 | Moon | H04W 4/80 |
| 2020/0178801 A1* | 6/2020 | Nazari | A61B 5/0031 |
| 2020/0382106 A1* | 12/2020 | Wang | H03K 3/0231 |

FOREIGN PATENT DOCUMENTS

| | | |
|---|---|---|
| KR | 1020050083662 A | 8/2005 |
| KR | 1020160060159 A | 5/2016 |
| KR | 1020180088156 A | 12/2018 |

OTHER PUBLICATIONS

Written Opinion dated Jul. 28, 2020, issued in corresponding International Application No. PCT/KR2020/005334, filed Apr. 22, 2020, 8 pages.

\* cited by examiner

GLUCOSE MEASUREMENT DEVICE AND METHOD

CROSS-REFERENCES TO RELATED APPLICATIONS

This is a continuation of International Application No. PCT/KR2020/005334, filed Apr. 22, 2020, which claims the benefits of Korean Patent Application No. 10-2019-0061153, filed May 24, 2019 and Korean Patent Application No. 10-2020-0048191, filed Apr. 21, 2020, the disclosures of which are each expressly incorporated herein by reference in their entirety.

BACKGROUND OF INVENTION

Field of Invention

The disclosure is associated with a medical device and is more particularly associated with a device and method for measuring blood glucose.

Description of Related Art

In order to manage diabetes of hundreds of millions of people throughout the world, the most basic thing is to measure glucose. Accordingly, a glucose measurement device is an important diagnostic device which is essential for diabetes patients.

Various glucose measurement devices are recently developed. However, the most common method is a method of gathering blood by pricking a finger and directly measuring a concentration of glucose within the blood. If an invasive method is used, there is a method of penetrating an invasive sensor into the skin, measuring a concentration of glucose for a given time, and measuring glucose by allowing the concentration to recognize an external reader. In contrast, a non-invasive method includes a method using an LED-PD.

BRIEF SUMMARY OF THE INVENTION

A glucose measurement device which is disposed under the skin of a subject and operates according to an embodiment includes a communication unit which wirelessly receives power and transmits measured biometric-related parameter; a clock recovery unit which recovers a frequency used for the wireless power reception of the communication unit; a direct frequency synthesizer which converts, into a first band frequency, the recovery frequency recovered by the clock recovery unit; a clock controller which divides the recovery frequency and inputs the divided frequencies into an injection locked oscillator as frequencies having specific intervals; the injection locked oscillator which receives the first band frequency and the frequencies having the specific intervals and outputs a second band frequency; and a measurement unit which has a biometric-related parameter varying in response to subcutaneous biometric information, wherein the biometric-related parameter of the measurement unit may be measured using the second band frequency.

The injection locked oscillator may supply, to the measurement unit, a signal having the second band frequency varying in a frequency unit having the specific interval so that the second band is swept.

The biometric-related parameter may include a resonant frequency of the measurement unit.

The glucose measurement device may further include an envelope detector which detects an envelope of a signal passing through the measurement unit; and a register which stores a frequency corresponding to maximum amplitude in the envelope detected by the envelope detector.

The communication unit may transmit, to an external device, frequency data indicative of the frequency which is stored in the register and corresponds to the maximum amplitude.

The communication unit may transmit, to an external device, modulation data modulated from frequency data.

A glucose measurement device according to an embodiment includes a communication unit receiving a biometric-related parameter from a glucose measurement device which measures the biometric-related parameter varying in response to biometric information; and a processor determining glucose information based on the biometric-related parameter, wherein the biometric-related parameter may include at least one of a scattering parameter of a resonance element having a pattern structure included in the glucose measurement device, a response curve according to the scattering parameter, and a resonant frequency of the resonance element.

If the biometric-related parameter includes the scattering parameter, the processor may determine a resonant frequency corresponding to a minimum value or maximum value of the scattering parameter during frequency sweeping and may determine a glucose level corresponding to the resonant frequency as the glucose information.

The processor may determine glucose information at current timing by correcting glucose information at previous timing using a difference between a biometric-related parameter at previous timing and a biometric-related parameter at current timing in response to a change in the biometric-related parameter.

A glucose measurement method performed by a device disposed under the skin of a subject may include the steps of wirelessly receiving, by a communication unit, power; recovering, by a clock recovery unit, a frequency used for the wireless power reception of the communication unit; converting, by a direct frequency synthesizer, a recovery frequency recovered by the clock recovery unit into a first band frequency; dividing, by a clock controller, the recovery frequency and inputting the divided frequencies into an injection locked oscillator with as frequencies having specific intervals; receiving, by the injection locked oscillator, the first band frequency and the frequencies having the specific intervals and outputting a second band frequency; and measuring a biometric-related parameter of a measurement unit varying in response to subcutaneous biometric information using the second band frequency.

The glucose measurement method may further include a step of transmitting the measured biometric-related parameter to an outside.

The glucose measurement method may further include the steps of detecting, by an envelope detector, an envelope of a signal passing through the measurement unit; and storing, by a register, a frequency corresponding to maximum amplitude in the envelope detected by the envelope detector.

DETAILED DESCRIPTION OF THE INVENTION

Figure 1:
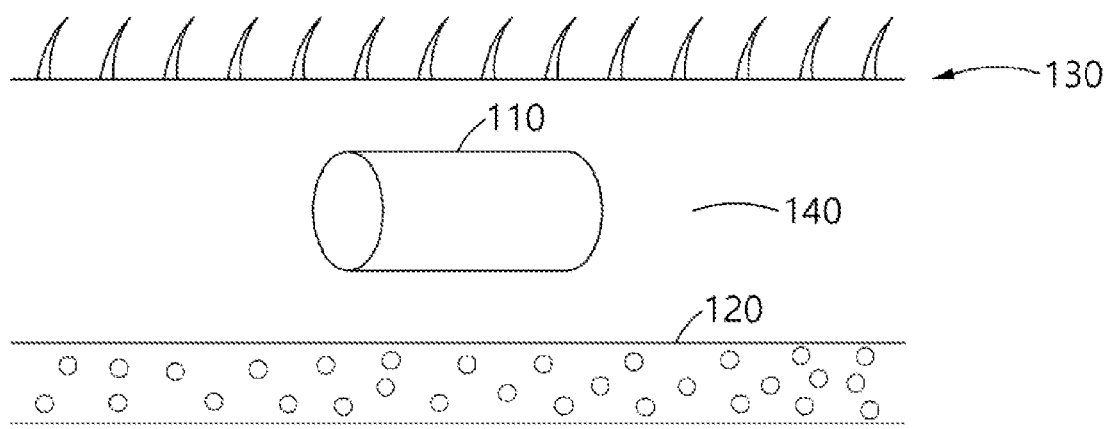
FIG. 1 illustrates a glucose measurement device disposed under the skin according to an embodiment.

Hereinafter, embodiments are described in detail with reference to the accompanying drawings. However, the scope of a right is not limited or restricted to such embodiments. The same reference numeral illustrated in each drawing denotes the same member.

Terms used in the following description are common and universal terms selected in an associated technical field, but may include other terms depending on the development and/or change of a technology, a practice, the preference of a technician, etc. Accordingly, the terms described in the following description should not be understood to restrict technical spirit and should be understood as illustrative terms for describing embodiments.

Furthermore, in a specific case, some terms are randomly selected by the applicant. In this case, the meaning of a corresponding term will be described in detail in the corresponding description of the invention. Accordingly, terms used in the present disclosure should be defined based on their substantial meanings and contents over the present disclosure, not the simple names of the terms.

FIG. 1 illustrates a glucose measurement device disposed under the skin of a subject according to an embodiment.

The biometric measurement device according to an embodiment may measure a biometric-related parameter. A biometric measurement device capable of measuring a biometric-related parameter of glucose may be indicated as the glucose measurement device 110. The glucose measurement device 110 may be disposed under the skin 130 of a subject not a blood vessel 120. For example, the glucose measurement device 110 does not have a direct contact with the blood or is not disposed within the blood vessel 120, but may be disposed in an area other than the blood vessel 120 at a shallow depth under the skin 130. In other words, the glucose measurement device 110 may be disposed in an area 140 under the skin the skin 130 and the blood vessel 120.

The glucose measurement device 110 according to an embodiment may measure a biometric-related parameter under the skin of a subject. The glucose measurement device 110 and/or an external device that establishes communication with the glucose measurement device 110 may determine biometric information using a biometric-related parameter. The biometric information is information related to biometric components of a subject, and may include a concentration, a numerical value, etc. of a target analyte, for example. If the target analyte is glucose, the biometric information may include a glucose level. The biometric-related parameter is a parameter related to the biometric information, and may indicate a parameter varying in response to a change in the biometric information and a parameter indicative of a change in the biometric information.

Biometric information related to glucose may be indicated as glucose information. Hereinafter, a glucose level is illustratively described as biometric information. For example, when a glucose level within the blood vessel 120 changes, a glucose level in the area 140 under the skin may change. Permittivity in the area 140 under the skin may change in response to a change in the glucose level. As will be described later with reference to FIG. 4, the glucose measurement device 110 may include a measurement unit having a resonant frequency vary in response to a change in the permittivity around the measurement unit. For example, the measurement unit may include a conducting wire having a specific pattern, a power feeder, etc. A resonant frequency by the specific pattern and the power feeder may change in response to a change in the permittivity around the measurement unit. The reason for this is that when the permittivity changes, capacitance of the measurement unit also changes. In this case, a biometric-related parameter may be a parameter related to the resonant frequency of the measurement unit. The biometric-related parameter may include a scattering parameter of the measurement unit (to be described later with reference to FIG. 4) included in a biometric measurement device (e.g., the glucose measurement device) and having a pattern structure, a response curve according to the scattering parameter, a resonant frequency corresponding to a minimum value or a maximum value in the response curve according to the scattering parameter, a resonant frequency corresponding to timing indicative of maximum amplitude in an envelope detected by an envelope detector, etc. The scattering parameter may also be indicated as an S parameter.

Accordingly, the glucose measurement device 110 may obtain a glucose level from a measured biometric-related parameter. For reference, in this specification, the glucose measurement device 110 is chiefly described for convenience of description, but the present disclosure is not limited thereto. Another type of biometric measurement device capable of measuring biometric information may operate identically with or similar to the glucose measurement device 110 described in this specification.

Figure 2:
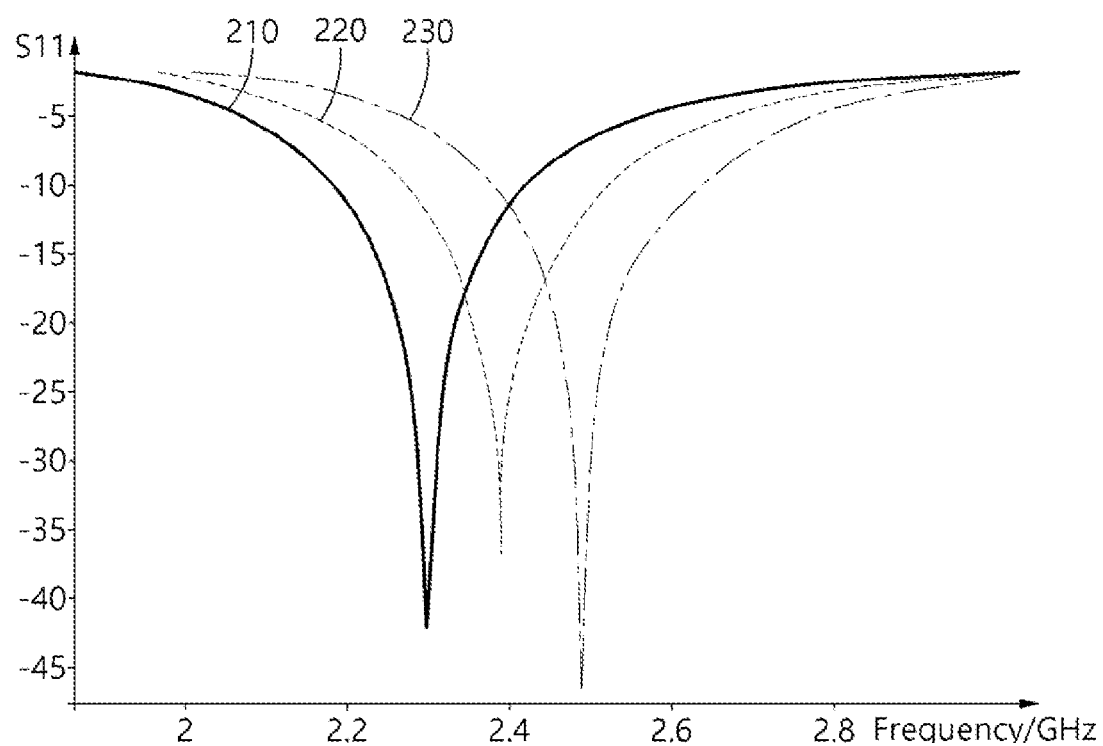
FIG. 2 is a graph illustrating a change in the scattering parameter, that is, a network response characteristic of a frequency for a change in the permittivity according to an embodiment.

FIG. 2 is a graph illustrating a change in the scattering parameter, that is, a network response characteristic of a frequency for a change in the permittivity according to an embodiment.

FIG. 2 illustrates, in a dB unit, a frequency varying in response to a change in the permittivity and the magnitude of an S11 parameter at that time. The glucose measurement device according to an embodiment may measure a frequency and a scattering parameter in response to a change in the permittivity. The network response characteristic may indicate a frequency response characteristic of a 2-port network.

FIG. 2 illustrates a response curve 210 in which a glucose concentration is 50, a response curve 220 in which a glucose concentration is 75, and a response curve 230 in which a glucose concentration is 100, illustratively, but without being limited thereto. Since the permittivity changes in response to a change in the glucose concentration, a graph form of the scattering parameter may change within a specific frequency band. Accordingly, a change in the glucose of a blood vessel around a subcutaneous area (e.g., a surrounding area where the glucose measurement device is disposed) may be determined based on an aspect of a change in the scattering parameter, which may be obtained by sweeping a signal having a specific frequency band.

Furthermore, since a glucose concentration under the skin changes in proportion to a glucose concentration of an adjacent blood vessel, a glucose level may be finally calculated using a resonant frequency corresponding to a change in the permittivity under the skin.

In an embodiment, when a frequency band changes in 2.2 GHz to 2.6 GHz, each graph may have a threshold. For example, the threshold may appear between 2.3 GHz and 2.5 GHz, but the frequency band is not limited thereto. A corresponding frequency is illustratively a resonant frequency, and may be a frequency corresponding to a point indicative of a minimum value or a maximum value among scattering parameter obtained during frequency sweeping.

FIG. 2 illustrates response curves, corresponding to the S11 parameter, as examples of the scattering parameter. A frequency having the smallest value of the S11 parameter may be a point corresponding to a resonant frequency, but the present disclosure is not limited thereto. If a biometric-related parameter is an S21 parameter, a frequency having the greatest value of the S21 parameter may be a point corresponding to a resonant frequency.

The glucose measurement device according to an embodiment may calculate a corresponding relative permittivity by using a frequency (e.g., a resonant frequency) at a point where the magnitude of a scattering parameter is the smallest or greatest, but the present disclosure is not limited thereto. The glucose measurement device and/or an external device that establishes communication with the glucose measurement device may determine a glucose level corresponding to a resonant frequency. The reason for this is that as described above, a glucose level corresponds to a relative permittivity and the relative permittivity corresponds to a resonant frequency of the measurement unit. The glucose measurement device will be described in detail with reference to FIG. 3.

Figure 3:
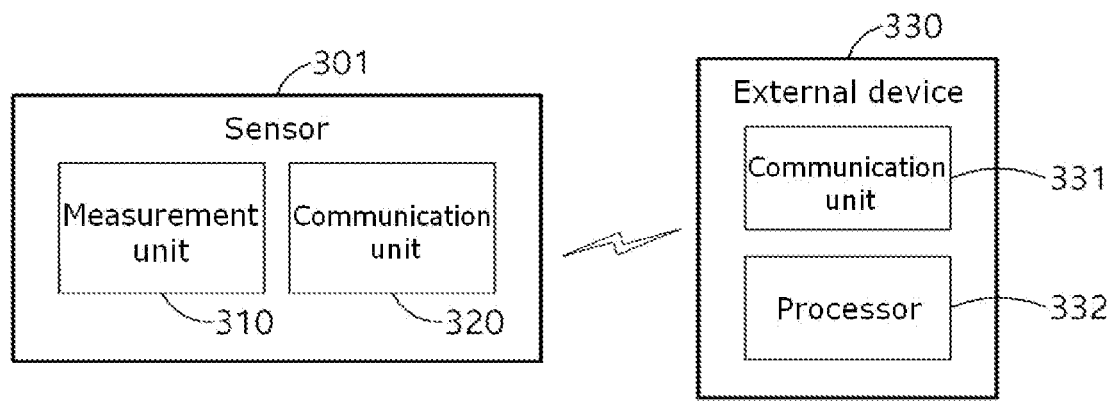
FIG. 3 is a block diagram illustrating a glucose measurement system according to an embodiment.

FIG. 3 is a block diagram illustrating a glucose measurement system according to an embodiment.

The glucose measurement system 300 according to an embodiment may include a sensor 301 and an external device 330. The sensor 301 may include a measurement unit 310 and a communication unit 320.

Illustratively, the sensor 301 illustrated in FIG. 3 may be disposed under the skin of a subject, and the external device 330 may be disposed outside the body of the subject.

The measurement unit 310 may be configured in the form of a resonance element illustratively, but without being limited thereto. The resonance element according to an embodiment is an element having a capacitance component and an inductance component. The capacitance component of the resonance element may be designed to vary in response to a change in surrounding biometric components. Accordingly, a resonant frequency of the resonance element may change in response to a change in the biometric components. The resonance element may indicate an antenna characteristic and/or a filter characteristic (e.g., a bandpass characteristic). For example, the resonance element may include a conducting wire having a pattern structure to be described later with reference to FIG. 4. The biometric components may include glucose, for example, but the present disclosure is not limited thereto. The sensor 301 may measure a biometric-related parameter of the measurement unit 310 (e.g., the resonance element). Specifically, the sensor 301 disposed under the skin of a subject may generate a signal by sweeping a frequency within a predetermined frequency band, and may inject the generated signal into the resonance element. The sensor 301 may measure a scattering parameter of the resonance element to which a signal having a varying frequency is supplied.

The communication unit 320 may transmit, to the external device 330, data indicative of a measured scattering parameter. Furthermore, the communication unit 320 may receive power for generating a signal supplied to the measurement unit 310 using a wireless power transmission method. The communication unit 320 may include a coil, and may wirelessly receive power or transmit data.

The external device 330 may include a communication unit 331 and a processor 332. The communication unit 331 of the external device 330 may receive a biometric-related parameter from the glucose measurement device that measures a biometric-related parameter varying in response to biometric information. For example, the communication unit 331 may receive biometric-related parameter data (e.g., a scattering parameter and a degree of a change in the resonant frequency) of the resonance element, which is measured with respect to the measurement unit 310. The processor 332 of the external device 330 may determine biometric information (e.g., a glucose level) by using the received biometric-related parameter.

The external device 330 may also be indicated as a biometric information processing device. A biometric information processing device that determines information indicative of glucose as biometric information may also be indicated as a glucose determination device. For example, the processor 332 of the external device 330 may store a look-up table (LUT) in which a corresponding glucose level has been previously mapped to each of values of biometric-related parameters, and may load a glucose level corresponding to a measured biometric-related parameter based on the LUT. For another example, the external device 330 may map a previous biometric-related parameter value (e.g., a resonant frequency value) to a previous glucose level (e.g., a glucose level of invasively obtained blood, which is measured by the electrochemical sensor 301) at given timing, and may store the mapping results. After the aforementioned timing, the external device 330 may also calculate a current glucose level by correcting the previous glucose level based on a difference between a current biometric parameter value and the previous biometric parameter value. The reason for this is that when a subcutaneous glucose concentration changes, the permittivity also changes because subcutaneous glucose increases when glucose of a blood vessel increases.

However, the present disclosure is not limited to such an example. The external device 330 may calculate a relative permittivity using biometric-related parameter data, and may calculate a glucose level of an adjacent blood vessel using the relative permittivity. Furthermore, the external device 330 may finally calculate a glucose level by using a correlation between the glucose level of the adjacent blood vessel and the relative permittivity. The correlation between the relative permittivity and the glucose level according to an embodiment may be indicated as in Table 1 below.

TABLE 1

| Relative permittivity ($\varepsilon_r$) | Glucose level (mg/dL) |
| --- | --- |
| 70.2 | 150 |
| 71.3 | 100 |
| 72.4 | 50 |
| 73.5 | 0 |

Table 1 illustrates measured values of glucose levels according to relative permittivities (or dielectric constants) under the skin. It can be seen that as the relative permittivity increases, the glucose level decreases in inverse proportion to the relative permittivity value. The external device 330 may calculate a glucose level using glucose level data according to a relative permittivity that has been previously measured as in the above table. Illustratively, the external device 330 may calculate a relative permittivity corresponding to a measured biometric-related parameter value of the measurement unit, and may calculate that glucose is 100 mg/dL when the relative permittivity value is 71.3. This is merely an example, and the present disclosure is not limited thereto. A measured value may be changed depending on a subject.

An example in which the sensor 301 transmits a biometric-related parameter to the external device 330 without processing the biometric-related parameter has been chiefly described, but the present disclosure is not limited thereto. For example, the sensor 301 further includes a processor therein. The processor of the sensor 301 may calculate a glucose level. In this case, the sensor 301 may transmit the calculated glucose level to the external device through the communication unit. Furthermore, an additional device (not illustrated) including a processor may be disposed under the skin, and may establish body communication with the sensor 301. In this case, the additional device (not illustrated) may directly receive measured biometric-related parameter data from the sensor 301, and may calculate a glucose level. Furthermore, the additional device may transmit the calculated glucose level to the external device 330 within the body of a subject.

The external device 330 may further include a display unit (not illustrated), and may display a calculated glucose level. The display unit may be disposed outside the body of a subject, and may receive a calculated glucose level and display the calculated glucose level. The display unit may receive a glucose level from the communication unit, and may display the glucose level as a number or in a graph form, but the present disclosure is not limited to an illustrated display format. The display unit may display glucose using various methods.

Figure 4:
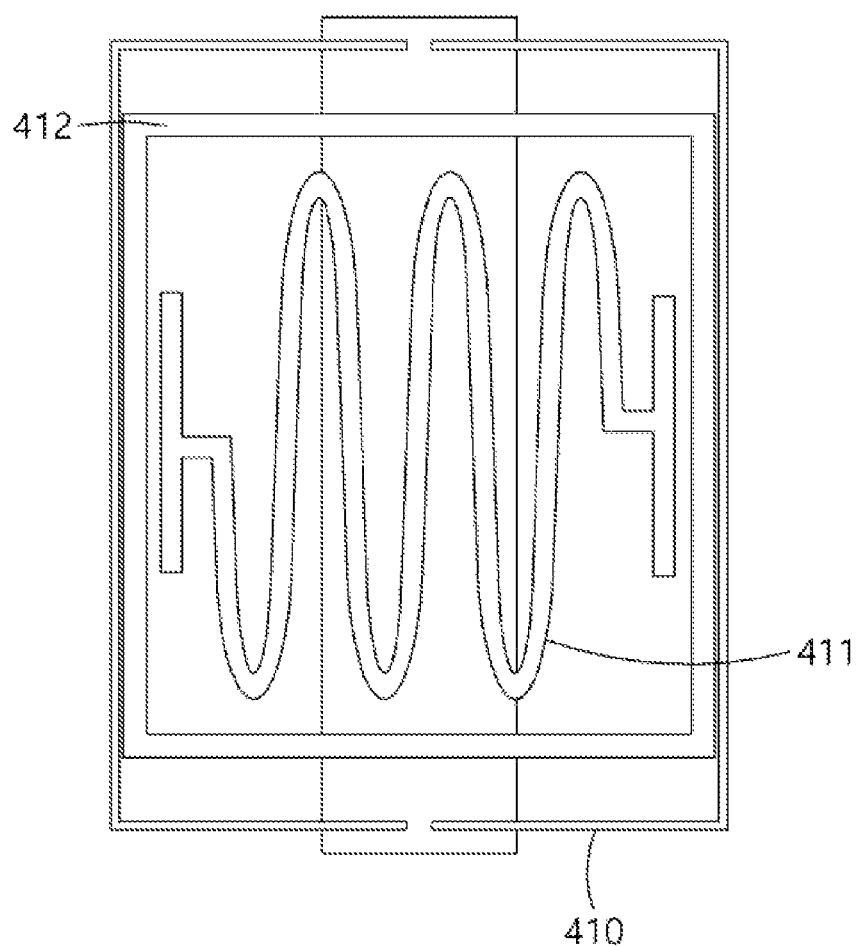
FIG. 4 illustrates a pattern structure of the measurement unit of the glucose measurement device according to an embodiment.

FIG. 4 illustrates a pattern structure of the measurement unit of the glucose measurement device according to an embodiment.

The measurement unit 400 of the glucose measurement device according to an embodiment may include a resonance element including a conducting wire having a pattern structure. For example, the measurement unit 400 may include a power feeder 410, a closed-loop conducting wire 412, and a pattern structure element 411. The measurement unit 400 may show a characteristic similar to a kind of band pass filter (BPF) by the power feeder 410, the closed-loop conducting wire 412, and the pattern structure element 411. The glucose measurement device may measure a scattering parameter indicative of the intensities of a signal input to the measurement unit 400 and a signal output by the measurement unit 400.

The pattern structure element 411 may be composed of a conducting wire having a pattern showing a sine wave form having three cycles illustrated in FIG. 4, for example. However, the specific pattern illustrated in FIG. 4 is merely illustrative, and the present disclosure is not limited thereto.

Figure 5:
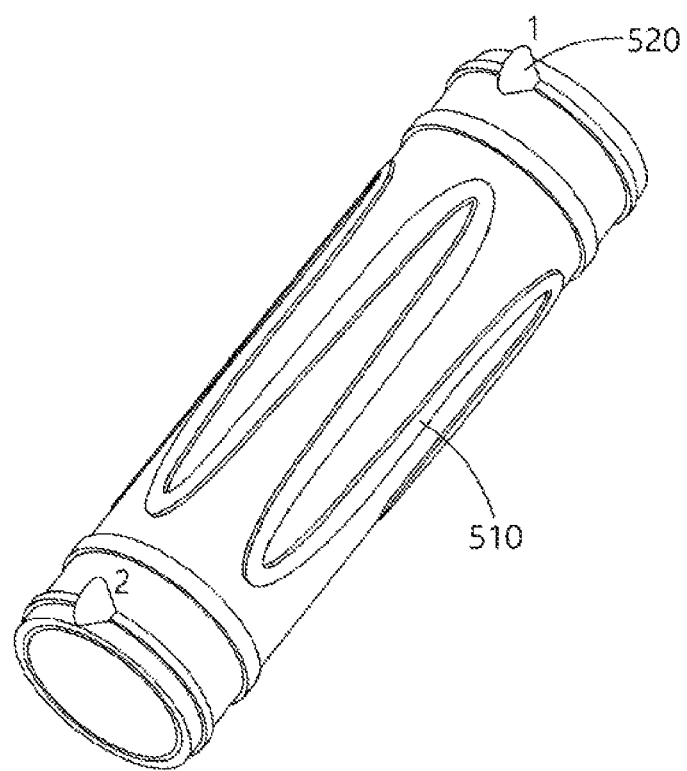
FIG. 5 illustrates the structure of a sensor of the glucose measurement device, which is inserted under the skin, according to an embodiment.

Moreover, the structure of the measurement unit 400 illustrated in FIG. 4 is illustrated in a plane form, but may be rolled like a form illustrated in FIG. 5 in order to be coupled to a glucose measurement device having a cylinder form. For example, the measurement unit 400 may be disposed to surround the side of a cylinder member.

FIG. 5 illustrates an overall structure of the glucose measurement device according to an embodiment.

The glucose measurement device according to an embodiment may be disposed in an area other than a blood vessel under the skin of a subject, and may include a measurement unit 510 and a communication unit.

The measurement unit 510 may have the same form as the measurement unit 400, illustrated in FIG. 4, when spread out, and may have the form, illustrated in FIG. 5, when rolled in a cylinder form.

According to an embodiment, a sensor (e.g., the glucose measurement device) may measure the intensities of a signal input to the measurement unit 510 and a signal output by the measurement unit 510 in a specific frequency band. For example, a signal having a second band frequency may be input to the power feeder 410 of FIG. 4 through the input port 520 of the measurement unit 510.

Measured data may be transmitted to the outside of the body of a subject through the communication unit.

The communication unit may further include a coil (not illustrated) for wireless power transmission. The coil may be disposed within a body having a cylinder form. Alternatively, a method of disposing the coil to surround the body having a cylinder form or separately disposing the coil outside the body having a cylinder form is available. Furthermore, the communication unit may use the coil when transmitting or receiving data.

Figure 6:
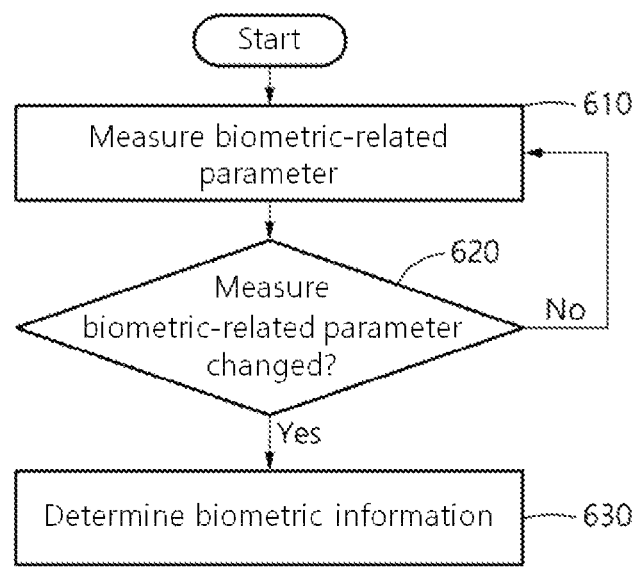
FIG. 6 is a flowchart illustrating a glucose measurement method according to an embodiment.

FIG. 6 is a flowchart illustrating a glucose measurement method according to an embodiment.

First, in step 610, the glucose measurement system may measure a biometric-related parameter. For example, the glucose measurement device (e.g., the sensor) may be disposed under the skin, and may measure a biometric-related parameter. If glucose is to be measured, the glucose measurement device is inserted under the skin of a subject. The glucose measurement device disposed under the skin may measure a biometric-related parameter.

The biometric-related parameter may be illustratively a scattering parameter of the measurement unit. The glucose measurement device may measure the intensities of a signal input to the measurement unit and a signal output therefrom in a predetermined frequency band. The predetermined frequency band may be a 2.2 to 2.6 GHz band. The glucose measurement device may measure the scattering parameter as a biometric-related parameter in the band. The glucose measurement device and/or an external device may calculate a glucose level using the biometric-related parameter.

Furthermore, in step 620, the glucose measurement system may determine whether the biometric-related parameter has changed. For example, the glucose measurement device and/or the external device may determine that the biometric-related parameter has changed in response to a case where a difference between a biometric-related parameter measured at previous timing and a biometric-related parameter measured at current timing is equal to or greater than a threshold difference. In response to a case where the biometric-related parameter is maintained, the glucose measurement device may return to step 610 and continue to measure a biometric-related parameter. In response to a case where the biometric-related parameter has changed, the glucose measurement device and/or the external device may determine biometric information in step 630.

Next, in step 630, the glucose measurement system may determine biometric information. For example, the glucose measurement device and/or the external device may determine the biometric information (e.g., a glucose level), corresponding to the measured biometric-related parameter, based on a look-up table. The look-up table may be a table in which a corresponding biometric-related parameter value has been matched with each biometric information value. The glucose measurement device and/or the external device may obtain, from the look-up table, a biometric information value corresponding to the measured biometric-related parameter value by searching for the biometric information value. For another example, the glucose measurement device and/or the external device may store a biometric-related parameter value measured at previous timing and a glucose level value at corresponding timing. The glucose measurement device and/or the external device may calculate a glucose level value at current timing by correcting a glucose level value at previous timing based on a difference between a biometric-related parameter value at previous timing and a biometric-related parameter value at current timing. The biometric information value at previous timing may be obtained using various methods (e.g., a method of a user directly inputting an electrochemically sensed value of invasively collected blood). When glucose within a blood vessel changes, glucose under the skin also changes in proportion thereto. At this time, a relative permittivity also changes. The glucose measurement system may measure a scattering parameter according to a change in the permittivity through the measurement unit, and may calculate a glucose value within the blood vessel using the measured S-parameter.

However, the present disclosure is not limited thereto. In step 630, the glucose measurement system may primarily calculate a relative permittivity using biometric-related parameter data. The S11 parameter of the measurement unit is changed in response to a frequency supplied to the measurement unit. At this time, a change pattern of the S11 parameter may differently appear depending on the relative permittivity under the skin. The change pattern according to the relative permittivity has been specifically described with reference to FIG. 2. Accordingly, if S11 parameter data varying in response to the frequency is used, the relative permittivity under the skin can be calculated. The glucose measurement system may calculate the relative permittivity by using the S11 parameter measured by the sensor. The glucose measurement system may finally calculate a glucose level by using the relative permittivity data. A change in the relative permittivity under the skin has a correlation with a change in the glucose level of an adjacent blood vessel. If the calculated relative permittivity is used, the glucose level can be finally calculated.

Figure 7:
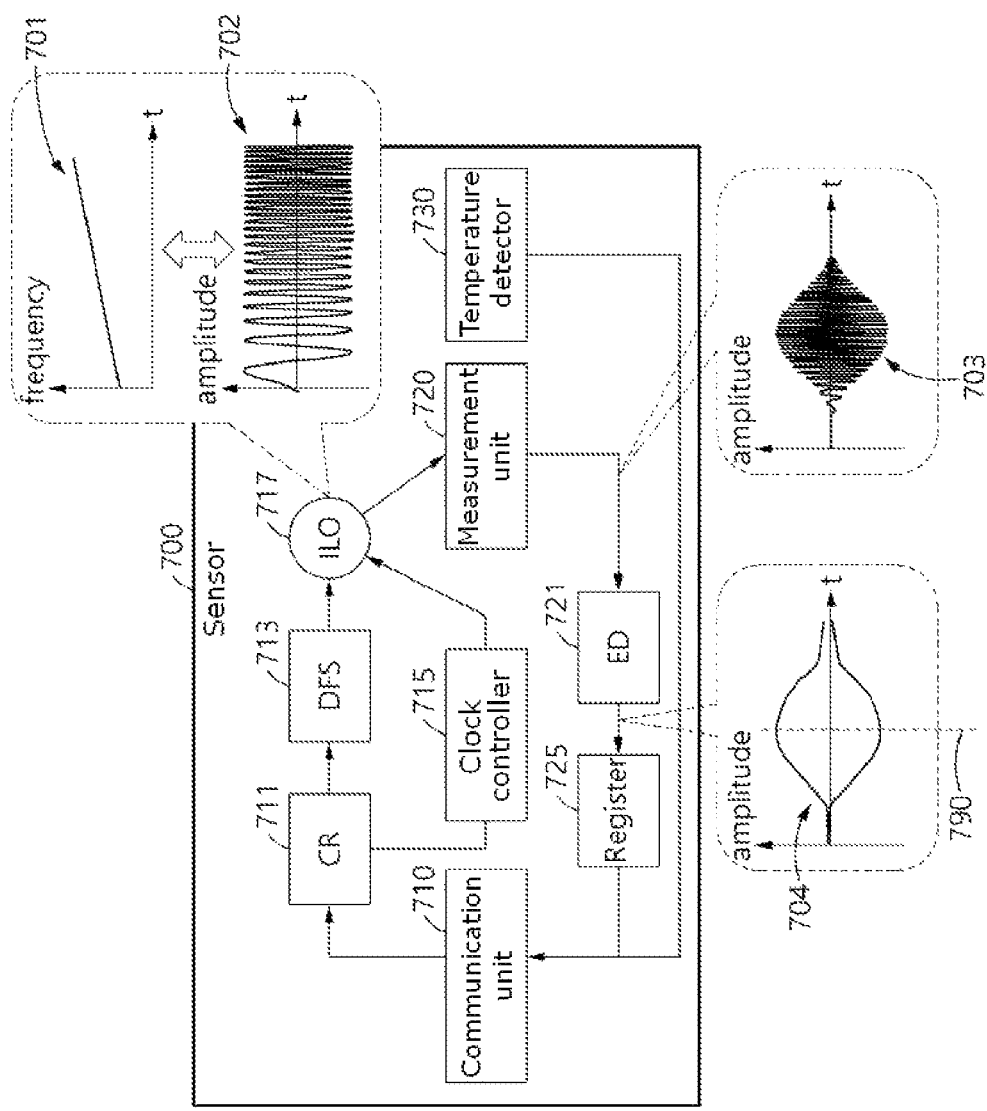
FIG. 7 is a block diagram more specifically illustrating a configuration of a sensor according to an embodiment.

FIG. 7 is a block diagram more specifically illustrating a configuration of a sensor according to an embodiment.

The sensor 700 according to an embodiment may include a communication unit 710, a clock recovery (CR) unit 711, a direct frequency synthesizer 713, a clock controller 715, an injection locked oscillator 717, a measurement unit 720, an envelope detector 721, a register 725, and a temperature detector 730.

The measurement unit 720 of the sensor 700 for measuring glucose according to an embodiment may have a characteristic in which a resonant frequency thereof is changed in response to relative permittivity around the sensor. Illustratively, the measurement unit 720 may have the structure illustrated in FIG. 4. For example, an input port (e.g., first port) of the measurement unit 720 may be connected to the injection locked oscillator 717, and an output port (e.g., second port) of the measurement unit 720 may be connected to the envelope detector 721.

In order to operate the sensor 700, a signal having a constantly changing frequency is injected. If such a signal is changed through the measurement unit 720, an interface circuit for measuring a change in the corresponding signal is required.

Specifically, in order to accurately generate a desired frequency, an accurate reference frequency is necessary. A crystal oscillator capable of generating an accurate reference frequency is too bulky and thus cannot be used on the nature of a characteristic (e.g., form factor restriction) of the proposed system implanted into the body.

The sensor according to an embodiment may use a frequency used in wireless power transmission. The frequency used in wireless power transmission may be illustratively 13.56 MHz, but is not limited thereto and may be changed by those skilled in the art.

In wireless power transmission, the intensity of power and the size of a voltage may be frequently changed depending on a load. However, a frequency for wireless power transmission may be used as a reference frequency because a value thereof is not changed. Operations of the elements are sequentially described.

The communication unit 710 may receive power from the outside using a wireless power transmission method, and may transmit measured data to the outside using wireless communication.

The clock recovery unit 711 may recover a frequency used for the communication unit 710 to receive wireless power. For example, the clock recovery unit 711 may recover a signal having a 13.56 MHz frequency using a signal received from the communication unit 710 through wireless power reception.

The direct frequency synthesizer 713 may raise, to a first band, a frequency generated by the recovery. The first band may be an 800 MHz band illustratively, but without being limited thereto.

The signal having the first band may be amplified through an amplifier. The injection locked oscillator 717 may generate a frequency having a second band from the amplified signal having the first band. The second band may be a frequency band including 2.35 GHz illustratively, but without being limited thereto.

According to another embodiment, the frequency having the second band, that is, a desired target band, can be directly obtained from a recovery frequency of 13.56 MHz using a phase locked loop (PLL) method without passing through the first band.

At this time, the clock controller 715 may sweep the second band by changing a frequency output by the injection locked oscillator 717 in a specific interval unit using a clock generated by the clock recovery unit 711. The frequency swept within the second band may be indicated as a second band frequency. For example, the clock controller 715 may sequentially increase or decrease a frequency by a frequency corresponding to a specific interval. Illustratively, the specific interval unit may be a 40 KHz unit. FIG. 7 illustrates a frequency 701 that linearly increases over time illustratively, but the frequency is only illustrative, and the present disclosure is not limited thereto.

A signal 702 having the frequency output by the injection locked oscillator 717 may have its power amplified by a power amplifier (PA), and may be input to the measurement unit 720. As described above, the resonance element of the measurement unit 720 may indicate a kind of bandpass filter characteristic. A band which may pass through the measurement unit 720 may be set based on a resonant frequency. In other words, since permittivity varies in response to a change in glucose, a band which may pass through the measurement unit 720 may be changed. Accordingly, if the output of the measurement unit 720 is amplified by a low noise amplifier (LNA), a signal 703 having a form similar to that of a signal that has passed through a bandpass filter may be obtained. Amplitude of the signal 703 passing through the measurement unit 720 may rise up to timing corresponding to the resonant frequency of the measurement unit 720, and may gradually decrease after the resonant frequency. The envelope detector 721 may detect an envelope signal 704 of the signal 703 passing through the measurement unit 720. A frequency, corresponding to timing 790 at which amplitude is a maximum in the detected envelope signal 704, may correspond to the resonant frequency of the measurement unit 720. Accordingly, the register 725 may store frequency data (e.g., data indicative of the resonant frequency) corresponding to the timing 790 at which amplitude is a maximum in the envelope signal 704. The frequency data may indicate data indicative of a frequency corresponding to maximum amplitude in the envelope signal. The communication unit 710 may transmit modulation data modulated from the frequency data. For example, finally, frequency data corresponding to the timing 790 at which maximum amplitude appears in the envelope signal may be transmitted to the outside through the communication unit 710 using modulation communication (e.g., load shift keying (LSK) or a modulation method equivalent thereto).

The external device communicating with the glucose measurement device implanted into the body may calculate a glucose level by receiving resonant frequency information. For example, the external device may determine a glucose level corresponding to a resonant frequency. For another example, the external device may calculate relative permittivity corresponding to a resonant frequency, and may calculate a glucose level matched with the relative permittivity. A relation between the resonant frequency and the relative permittivity and a relation between the relative permittivity and glucose are the same as those described in Table 1, etc. The glucose measurement device implanted into the body can measure glucose safely and conveniently through the series of processes.

According to another embodiment, a biometric-related parameter may be the S21 parameter. For example, the S21 parameter and permittivity in the biometric-related parameter may be represented in a form of a graph different from that of the S11 parameter and permittivity. If the measurement unit is composed of a 2-port network, the S21 parameter may mean a ratio of the intensity of a signal output by the output port of the measurement unit and the intensity of a signal input to the input port thereof. A relation between the S21 parameter and the permittivity may be analyzed using the measurement unit including the resonance element illustratively, but without being limited thereto.

The temperature detector 730 may measure a temperature under the skin. The communication unit 710 may transmit, to an external device, the temperature measured by the temperature detector 730. The external device may correct biometric information using the measured temperature. Accordingly, the external device may compensate for an error of the biometric information attributable to a temperature variation.

The aforementioned device may be implemented by a hardware component, a software component and/or a combination of a hardware component and a software component. For example, the device and components described in the embodiments may be implemented using one or more general-purpose computers or special-purpose computers, like a processor, a controller, an arithmetic logic unit (ALU), a digital signal processor, a microcomputer, a field programmable gate array (FPGA), a programmable logic unit (PLU), a microprocessor or any other device capable of executing or responding to an instruction. The processing device may perform an operating system (OS) and one or more software applications executed on the OS. Furthermore, the processing device may access, store, manipulate, process and generate data in response to the execution of software. For convenience of understanding, one processing device has been illustrated as being used, but a person having ordinary skill in the art may understand that the processing device may include a plurality of processing elements and/or a plurality of types of processing elements. For example, the processing device may include a plurality of processors or a single processor and a single controller. Furthermore, a different processing configuration, such as a parallel processor, is also possible.

Software may include a computer program, a code, an instruction or a combination of one or more of them and may configure a processing device so that the processing device operates as desired or may instruct the processing devices independently or collectively. The software and/or the data may be embodied in any type of machine, component, physical device, virtual equipment or computer storage medium or device in order to be interpreted by the processor or to provide an instruction or data to the processing device. The software may be distributed to computer systems connected over a network and may be stored or executed in a distributed manner. The software and the data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure alone or in combination. The program instructions stored in the medium may be specially designed and constructed for the present disclosure, or may be known and available to those skilled in the field of computer software. Examples of the computer-readable storage medium include magnetic media such as a hard disk, a floppy disk and a magnetic tape, optical media such as a CD-ROM and a DVD, magneto-optical media such as a floptical disk, and hardware devices specially configured to store and execute program instructions such as a ROM, a RAM, and a flash memory. Examples of the program instructions include not only machine language code that is constructed by a compiler but also high-level language code that can be executed by a computer using an interpreter or the like. The hardware device may be configured to operate as one or more software modules for executing the operation of the embodiment, and the vice versa.

As described above, although the embodiments have been described in connection with the limited embodiments and drawings, those skilled in the art may modify and change the embodiments in various ways from the description. For example, proper results may be achieved although the above descriptions are performed in order different from that of the described method and/or the aforementioned components, such as a system, a configuration, a device, and a circuit, are coupled or combined in a form different from that of the described method or replaced or substituted with other components or equivalents.

Accordingly, other implementations, other embodiments, and equivalents of the claims fall within the scope of the claims.

The invention claimed is:

1. A glucose measurement device configured to be disposed under the skin of a subject and operates, comprising:
   a communication circuit which wirelessly receives power;
   a clock recovery circuit which recovers a frequency used for the wireless power reception of the communication circuit;
   a direct frequency synthesizer which converts, into a first band frequency, the recovery frequency recovered by the clock recovery circuit;
   a clock controller which divides the recovery frequency into divided frequencies and inputs the divided frequencies into an injection locked oscillator as frequencies having specific intervals;
   wherein the injection locked oscillator receives the first band frequency and the frequencies having the specific intervals and outputs a second band frequency; and
   a measurement circuit which measures a biometric-related parameter varying in response to subcutaneous biometric information, wherein the biometric-related parameter of the measurement unit is measured using the second band frequency.

2. The glucose measurement device of claim 1, wherein the injection locked oscillator supplies, to the measurement circuit, a signal having the second band frequency varying in a frequency unit having the specific interval so that the second band is swept.

3. The glucose measurement device of claim 1, wherein the biometric-related parameter comprises a resonant frequency of the measurement circuit.

4. The glucose measurement device of claim 1, further comprising: an envelope detector which detects an envelope of a signal passing through the measurement circuit; and a register which stores a frequency corresponding to a maximum amplitude in the envelope detected by the envelope detector.

5. The glucose measurement device of claim 4, wherein the communication circuit transmits, to an external device, frequency data indicative of the frequency stored in the register and corresponding to the maximum amplitude.

6. The glucose measurement device of claim 4, wherein the communication circuit transmits, to an external device, modulation data modulated from frequency data.

7. A glucose measurement method performed by a device configured to be disposed under the skin of a subject, comprising:
   wirelessly receiving, by a communication circuit, power;
   recovering, by a clock recovery circuit, a frequency used for the wireless power reception of the communication circuit;
   converting, by a direct frequency synthesizer, a recovery frequency recovered by the clock recovery circuit into a first band frequency;
   dividing, by a clock controller, the recovery frequency into divided frequencies and inputting the divided frequencies into an injection locked oscillator as frequencies having specific intervals;
   receiving, by the injection locked oscillator, the first band frequency and the frequencies having the specific intervals and outputting a second band frequency; and
   measuring a biometric-related parameter of a measurement circuit varying in response to subcutaneous biometric information using the second band frequency.

8. The glucose measurement method of claim 7, further comprising transmitting the measured biometric-related parameter to a location outside the skin of the subject.

9. The glucose measurement method of claim 7, further comprising: detecting, by an envelope detector, an envelope of a signal passing through the measurement circuit: and storing, by a register, a frequency corresponding to maximum amplitude in an envelope detected by the envelope detector.

* * * * *